United States Patent [19]

Karol et al.

[11] Patent Number: 5,194,621

[45] Date of Patent: Mar. 16, 1993

[54] ETHER DERIVATIVES OF 2,5-DIMERCAPTO-1,3,4-THIADIAZOLES

[75] Inventors: Thomas J. Karol; Robert J. Luo, both of Norwalk, Conn.

[73] Assignee: R. T. Vanderbilt Company, Inc., Norwalk, Conn.

[21] Appl. No.: 702,578

[22] Filed: May 20, 1991

[51] Int. Cl.$^5$ .................. C07D 417/12; C10M 1/38
[52] U.S. Cl. .................... 548/142; 252/47.5
[58] Field of Search ............ 548/142; 252/47.5

[56] References Cited

U.S. PATENT DOCUMENTS

| | | | |
|---|---|---|---|
| 2,850,453 | 9/1958 | Fields | 252/32.7 |
| 3,980,573 | 9/1976 | Okorodudu | 252/46.7 |
| 4,410,703 | 10/1983 | Okorodudu | 548/142 |
| 4,432,847 | 2/1984 | Fields | 204/158 R |
| 4,740,454 | 4/1988 | Deguchi | 548/142 |

FOREIGN PATENT DOCUMENTS 0943790 6/1956 Fed. Rep. of Germany.

*Primary Examiner*—Robert Gerstl
*Attorney, Agent, or Firm*—Rasma B. Balodis

[57] ABSTRACT

Disclosed are novel compounds prepared by reacting mono- or disulfide dimers of 2,5-dimercapto-1,3,4-thiadiazole with an aliphatic or aromatic alcohol and aldehyde. The compounds are effective antiwear agents and antioxidants when incorporated into lubricating compositions.

7 Claims, No Drawings

ETHER DERIVATIVES OF 2,5-DIMERCAPTO-1,3,4-THIADIAZOLES

BACKGROUND OF THE INVENTION

The present invention concerns novel ether derivatives of 2,5-dimercapto-1,3,4-thiadiazoles and their use as multifunctional additives in lubricating compositions.

Lubricating compositions ordinarily are formulated with various additives to enhance their performance. A problem sometimes encountered is that of compatibility between the various additives used. Therefore, it is desirable to use lubricating additives that can perform different functions.

Generally, lubricants contain additives known as antiwear agents which increase the load-carrying capacity of lubricants. The antiwear additives promote the formation of a surface film and thereby prevent wear of the contacting metal surfaces. During the course of use, lubricants are susceptible to deterioration due to oxidation. The oxidative process leads to the loss of lubricating properties and inadequate protection of the device to be lubricated. Antioxidants are added to inhibit the oxidative process. Therefore, it is desirable that antiwear agents possess antioxidant properties.

The most commonly used additives possessing both antiwear and antioxidant properties are zinc dihydrocarbylphosphorodithioates and heavy metal dihydrocarbyldithiocarbamates. However, due to stricter environmental controls, it is particularly desirable to reduce the phosphorus and heavy metal content in lubricants. There is a need to develop improved lubricating compositions that are environmentally sound. German Pat. No. 943,790 describes ashless 1,3,4-thiadiazole derivatives that improve the film strength under high load.

It has been surprisingly discovered that the foregoing disadvantages of the prior art lubricants can be eliminated by replacing all or part of the metal additives with certain ashless multifunctional ether derivatives of 2,5-dimercapto-1,3,4-thiadiazoles.

SUMMARY OF THE INVENTION

In accordance with the invention, there are provided novel 1,3,4-thiadiazole compounds characterized by the structural formula

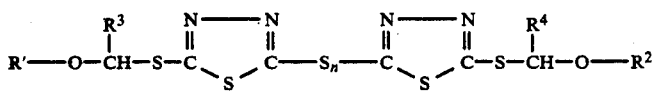

wherein n=1 to 2, R' represents alkyl having 1 to 20 carbon atoms, phenyl and alkyl substituted phenyl, $R^2$, $R^3$, and $R^4$ may be same or different and represent hydrogen, alkyl having 1 to 20 carbon atoms, phenyl and alkyl substituted phenyl, and mixtures thereof.

Another aspect of the invention concerns improved oil-based lubricating compositions comprising a major amount of base oil and an effective amount to impart antiwear and antioxidant properties to said composition, of a 1,3,4-thiadiazole characterized by the formula I.

A further aspect of the invention concerns a method for protection of metal surfaces from wear by applying improved lubricating oil or grease compositions, the improvement of which consists of adding to the composition an effective amount of a 1,3,4-thiadiazole characterized by the structural formula I.

DESCRIPTION OF SPECIFIC EMBODIMENTS

The novel compounds of the invention may be prepared by reacting mono-or disulfide dimers of 2,5-dimercapto-1,3,4-thiadiazole with an alcohol and aldehyde. If two different alcohols are used, mixed isomeric ethers may form. Excess alcohol may be used which serves as a solvent media for the reaction. If desired, a different inert solvent may be used as for example hexane and heptane. The dimers are commercially available. The mono-sulfide dimer is available under the trade name VANLUBE® RD-882A and the disulfide dimer as VANLUBE 829, both manufactured by R. T. Vanderbilt Company, Inc. The aliphatic and aromatic alcohol and aldehyde reactants are well known commercial materials.

The alkyl groups in formula I may be selected from straight and branched chain alkyls. Preferred are alkyl groups having 1 to 8 carbon atoms in the chain. The groups include, among others, methyl, ethyl, propyl, butyl, isobutyl, 2-heptyl, 2-ethylhexyl, and octyl. The phenyl group may be substituted by alkyl groups. Representative groups include, among others, 2,5-t-butylphenyl, octylated and nonylated phenyl groups.

The thiadiazole derivatives of the invention are useful as additives for industrial lubricating compositions and engine oil formulations.

The thiadiazole compounds possess multifunctional properties. They perform antiwear and oxidation inhibiting functions and impart load carrying properties in lubricants.

The lubricating compositions contemplated herein include lubricating oils, engine oils and lubricating greases containing a major amount of base oil. The base oil may be selected from naphthenic, aromatic, paraffinic, mineral and synthetic oils. The synthetic oils may be selected from, among others, alkylene polymers, polysiloxanes, carboxylic acid esters and polyglycol ethers.

The amount of the thiadiazole additive required to be effective for imparting antiwear and antioxidant characteristics to lubricating compositions may range from about 0.01 to 10.0 percent of the lubricating composition. The preferred range is about 0.1 to 5.0 percent of the additive based on the lubricating composition.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

A reactor was charged with 5,5'-dithiobis-1,3,4-thiadiazole-2(3H)-thione, 20 g (0.0671 moles), 2-ethylhexanol, 17.5 g (0.134 moles) and mixed with hexane, about 10 ml. After addition of benzaldehyde, 14 g (0.132 moles), the reactor was fitted with Dean Stark attachment filled with 10 ml hexane and the reaction was heated to remove water and solvent. The liquid product was filtered.

EXAMPLE 2

A reactor was charged with 5,5'-thiobis-1,3,4-thiadiazole-2(3H)-thione, 60 g (0.226 moles), propanol, 120 ml and acetaldehyde, 20 g (0.454 moles). The reaction was heated to reflux at 90°-92° C. for 2 hours. A Dean Stark attachment filled with hexane was used to remove water and some excess propanol which served as solvent. The remainder of the solvent was stripped off and the product was filtered through a filter aid.

EXAMPLE 3

A reactor with a Dean Stark trap was charged with 2,5-dimercapto-1,3,4-thiadiazole dimer, propanol and 2-ethylhexanol in the gram mole ratio of 1:1:1 and mixed with hexane, about 10 ml. Propylaldehyde, 2.3 gram moles, was added and refluxed. After removal of water, the reaction was maintained at 125° to 130° C. for one hour. The product was vacuum stripped and filtered through filter aid. The product, an isomeric ether mixture, was a clear brown liquid.

Using the above synthesis methods, compounds of Formula I were prepared as characterized in Table I:

TABLE I

| Compound | R¹ | R² | R³ | R⁴ | n |
|---|---|---|---|---|---|
| 1 | Butyl | Butyl | Isopropyl | Isopropyl | 1 |
| 2 | Propyl | Propyl | Ethyl | Ethyl | 2 |
| 3 | Butyl | Butyl | Ethyl | Ethyl | 2 |
| 4 | Propyl | Propyl | Isopropyl | Isopropyl | 2 |
| 5 | Butyl | Butyl | Isopropyl | Isopropyl | 2 |
| 6 | 2-Ethylhexyl | 2-Ethylhexyl | 2-Heptyl | 2-Heptyl | 2 |
| 7 | Isobutyl | Isobutyl | Phenyl | Phenyl | 2 |
| 8 | 2-Ethylhexyl | 2-Ethylhexyl | Phenyl | Phenyl | 2 |
| 9 | Butyl | Butyl | H | H | 2 |
| 10 | Isobutyl | Isobutyl | H | H | 2 |
| 11 | 3-Methylbutyl | 3-Methylbutyl | H | H | 2 |
| 12 | Isopropyl | Isopropyl | Methyl | Methyl | 2 |
| 13 | Isobutyl | Isobutyl | Methyl | Methyl | 2 |
| 14 | Butyl | Butyl | H | H | 1 |
| 15 | Isobutyl | Isobutyl | H | H | 1 |
| 16 | Propyl | Propyl | Methyl | Methyl | 1 |
| 17 | Propyl | Propyl | Ethyl | Ethyl | 1 |
| 18 | Propyl | Propyl | Ethyl | Methyl | 2 |
| 19 | Propyl | Propyl | Ethyl | Methyl | 1 |
| 20 | Propyl or 2-Ethylhexyl | 2-Ethylhexyl or propyl | Ethyl | Ethyl | 1 |
| 21 | Propyl or 2-Ethylhexyl | 2-Ethylhexyl or Propyl | Ethyl | Ethyl | 2 |

EXAMPLE 4

Four-Ball Wear Test

The wear preventive characteristics of additives of the invention were tested in lithium 12-OH stearate grease essentially according to the method described in ASTM D 2266-86. Four highly polished steel balls 12.7 mm in diameter were placed in the tester and about 5 g test sample was placed in the ball pot. The test was conducted at a rotation speed of 1200 rpm under a load of 40 kg at 75° C. The minimum scar diameter was measured to the nearest 0.01 mm.

The grease contained additives of the invention identified in Table I and referenced in Table II.

TABLE II

| | Four-Ball Wear Test | | |
|---|---|---|---|
| Sample | Active Ingredient | Percent | Scar Diameter, mm |
| A | — | — | 0.70 |
| B | Compound 13 | 2 | 0.59 |
| C | Compound 13 | 1 | 0.61 |
| D | Compound 16 | 1 | 0.57 |
| E | Compound 2 | 1 | 0.59 |
| F | Compound 17 | 1 | 0.55 |
| G | Compound 7 | 1 | 0.58 |

EXAMPLE 5

Four-Ball Wear Test

The wear preventive characteristics of additives of the invention were tested in polyol ester based fluid essentially according to the method described in ASTM D 4172. Four highly polished steel balls 12.7 mm in diameter were placed in the tester and about 5 g test sample was placed in the ball pot. The test was conducted at a rotation speed of 1800 rpm under a load of 20 kg for 1 hour at 54.4° C. The minimum scar diameter was measured to the nearest 0.01 mm.

The polyol ester contained isomeric additives of the invention identified in Table I and referenced in Table III.

TABLE III

| Sample | Active Ingredient | Percent | Scar Diameter, mm |
|---|---|---|---|
| H | — | — | 0.83 |
| I | Compound 20 | 0.1 | 0.43 |
| J | Compound 21 | 0.1 | 0.43 |

EXAMPLE 6

Extreme-Pressure Tests

The load carrying properties of lithium 12-OH stearate grease containing the compounds of the invention were tested essentially according to the method described in ASTM D 2596-87, the test was conducted at a rotating speed of 1800 rpm at 27°±8° C. The test samples were subjected to a series of tests of 10 second duration at increasing loads until welding of the balls occurred. The weld point measured in kgf indicates that the extreme-pressure level of the grease has been exceeded.

In a second test, the load-carrying capacity of the grease was determined by the Timken method conducted essentially according to the ASTM D2509-86 procedure. The tester was operated with a steel cup rotating against a steel test block at 800 rpm and about 24° C. Wear, indicated by seizure or welding of the two test pieces, was measured in kg after 10 min. The test samples contained additives of the invention identified in Table I and referenced in Table IV.

TABLE IV

Extreme-Pressure Test

| Sample | Active Ingredient | Percent | Weld Point, kgf | Timken, kg |
|---|---|---|---|---|
| K | — | — | 160 | 4.5 |
| L | Compound 13 | 1 | 315 | 22.7 |
| M | Compound 13 | 2 | 400 | 31.8 |
| N | Compound 16 | 2 | 400 | 22.7 |
| O | Compound 16 | 3 | 500 | 22.7 |
| P | Compound 2 | 2 | 400 | 20.4 |
| Q | Compound 2 | 3 | 400 | 22.7 |
| R | Compound 4 | 1 | 315 | 18.1 |
| S | Compound 8 | 1 | 250 | 13.6 |
| T | Compound 6 | 1 | 250 | 20.4 |
| U | Compound 20 | 2 | 250 | 31.8 |
| V | Compound 21 | 1 | 250 | 27.2 |

The above embodiments have shown various aspects of the present invention. Other variations will be evident to those skilled in the art and such modifications are intended to be within the scope of the invention as defined by the appended claims.

What is claimed is:

1. A thiadiazole compound selected from the group of compounds having the structural formula

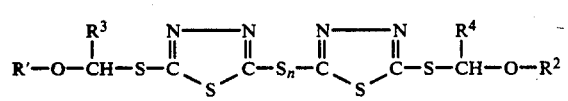

wherein n=1, R' represents alkyl having 1 to 20 carbon atoms, phenyl and alkyl substituted phenyl, $R^2$, $R^3$ and $R^4$ may be same or different and represent hydrogen, alkyl having 1 to 20 carbon atoms, phenyl and alkyl substituted phenyl, and mixture thereof.

2. A lubricating composition comprising a major portion of natural or synthetic oil of lubricating viscosity and a minor antiwear and oxidation inhibiting amount of a compound selected from the group consisting of compounds having the structural formula

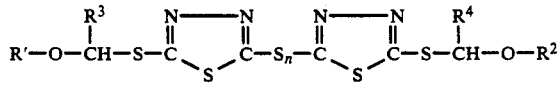

wherein n=1 to 2, R' represents alkyl having 1 to 20 carbon atoms, phenyl and alkyl substituted phenyl, R', $R^3$ and $R^4$ may be same or different and represent hydrogen, alkyl having 1 to 20 carbon atoms, phenyl and alkyl substituted phenyl, and mixtures thereof.

3. A lubricating composition of claim 2 which further contains a thickener.

4. A composition according to claim 2 wherein the antiwear and oxidation inhibiting compound has the structural formula wherein R' and $R^2$ are propyl and $R^3$ and $R^4$ are ethyl groups.

5. A composition according to claim 2 wherein the antiwear and oxidation inhibiting compound has the structural formula wherein R' and $R^2$ are 2-ethylhexyl and $R^3$ and $R^4$ are 2-heptyl groups.

6. A composition according to claim 2 wherein the antiwear and oxidation inhibiting compound has the structural formula wherein R' and $R^2$ are mixed propyl or 2-ethylhexyl and $R^3$ and $R^4$ are ethyl groups.

7. A method for protecting metal surfaces from wear which comprises contacting the surfaces with a lubricating composition comprising a major amount of base oil of lubricating viscosity, the improvement of which consists of adding to the oil a minor antiwear and oxidation inhibiting amount of an additive selected from the group of compounds having the structural formula

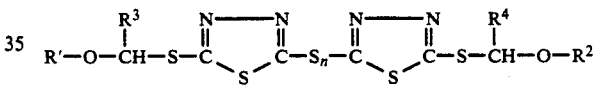

wherein n=1 to 2, R' represents alkyl having 1 to 20 carbon atoms, phenyl and alkyl substituted phenyl, $R^2$, $R^3$ and $R^4$ may be same or different and represent hydrogen, alkyl having 1 to 20 carbon atoms, phenyl and alkyl substituted phenyl, and mixtures thereof.

* * * * *

UNITED STATES PATENT AND TRADEMARK OFFICE
CERTIFICATE OF CORRECTION

PATENT NO. : 5,194,621
DATED : March 16, 1993
INVENTOR(S) : Thomas J. Karol and Robert J. Luo It is certified that error appears in the above-identified patent and that said Letters Patent is hereby corrected as shown below:

At col. 4, Table II, line 13 " B Ccnpound 13 "

should be -- B Compound 13 -- ;

At col. 6, lines 7 to 8 "R', $R^3$ and $R^4$ "

should be -- $R^2$, $R^3$ and $R^4$ -- .

Signed and Sealed this

Twenty-third Day of November, 1993

Attest:

BRUCE LEHMAN

*Attesting Officer*     *Commissioner of Patents and Trademarks*